United States Patent
Lyu

(10) Patent No.: US 12,175,563 B2
(45) Date of Patent: Dec. 24, 2024

(54) MULTI-SLICE MAGNETIC RESONANCE IMAGING METHOD AND DEVICE BASED ON LONG-DISTANCE ATTENTION MODEL RECONSTRUCTION

(71) Applicant: SHENZHEN TECHNOLOGY UNIVERSITY, Guangdong (CN)

(72) Inventor: Mengye Lyu, Guangdong (CN)

(73) Assignee: SHENZHEN TECHNOLOGY UNIVERSITY

( * ) Notice: Subject to any disclaimer, the term of this patent is extended or adjusted under 35 U.S.C. 154(b) by 410 days.

(21) Appl. No.: 17/845,198

(22) Filed: Jun. 21, 2022

(65) Prior Publication Data
US 2023/0097417 A1 Mar. 30, 2023

(30) Foreign Application Priority Data
Sep. 27, 2021 (CN) .......................... 202111138087.5

(51) Int. Cl.
*G06T 11/00* (2006.01)
*A61B 5/055* (2006.01)
(Continued)

(52) U.S. Cl.
CPC ........ *G06T 11/005* (2013.01); *G01R 33/4835* (2013.01); *G01R 33/5608* (2013.01);
(Continued)

(58) Field of Classification Search
CPC . G06T 11/005; G06T 11/006; G01R 33/4835; G01R 33/5608; G06N 3/08
See application file for complete search history.

(56) References Cited

FOREIGN PATENT DOCUMENTS

| CN | 105467339 A | 4/2016 |
| CN | 111856363 A | 10/2020 |

OTHER PUBLICATIONS

Wang, Dan, Xinrui Cui, Xun Chen, Zhengxia Zou, Tianyang Shi, Septimiu Salcudean, Z. Jane Wang, and Rabab Ward. "Multi-view 3d reconstruction with transformers." In Proceedings of the IEEE/CVF international conference on computer vision, pp. 5722-5731. 2021. (Year: 2021).*

(Continued)

*Primary Examiner* — David Perlman
(74) *Attorney, Agent, or Firm* — Jose Cherson Weissbrot

(57) ABSTRACT

The invention provides a multi-slice magnetic resonance imaging method and device based on long-distance attention model reconstruction. The method includes that: a deep learning reconstruction model is constructed; data preprocessing is performed on multiple slices of simultaneously acquired signals, and multiple slices of magnetic resonance images or K-space data is used as data input; learnable positional embedding and imaging parameter embedding are acquired; the preprocessed input data, the positional embedding and the imaging parameter embedding are input into the deep learning reconstruction model; and the deep learning reconstruction model outputs a result of the magnetic resonance reconstruction image. The invention further provides a device for implementing the method. The invention may improve the quality of the magnetic resonance image, improve the diagnosis accuracy of a doctor, increase the imaging speed, and improve the utilization rate of a magnetic resonance machine.

15 Claims, 4 Drawing Sheets

(51) Int. Cl.
*G01R 33/483* (2006.01)
*G01R 33/56* (2006.01)
*G06N 3/08* (2023.01)

(52) U.S. Cl.
CPC .............. *G06N 3/08* (2013.01); *G06T 11/006* (2013.01); *A61B 5/055* (2013.01); *G06T 2210/41* (2013.01); *G06T 2211/424* (2013.01)

(56) References Cited

OTHER PUBLICATIONS

Zanfir, M., Zanfir, A., Bazavan, E. G., Freeman, W. T., Sukthankar, R., & Sminchisescu, C. (2021). Thundr: Transformer-based 3d human reconstruction with markers. In Proceedings of the IEEE/CVF International Conference on Computer Vision (p. 12971-12980). (Year: 2021).*

Shen, Z., Yang, H., Zhang, Z., & Zheng, S. (2021). Automated kidney tumor segmentation with convolution and transformer network . In International Challenge on Kidney and Kidney Tumor Segmentation (pp. 1-12). Cham: Springer International Publishing. (Year: 2021).*

Yan, C., Shi, G., & Wu, Z. (2021, November). SMIR: A Transformer-Based Model for MRI super-resolution reconstruction. In 2021 IEEE International Conference on Medical Imaging Physics and Engineering (ICMIPE) (pp. 1-6). IEEE. (Year: 2021).*

\* cited by examiner

MULTI-SLICE MAGNETIC RESONANCE IMAGING METHOD AND DEVICE BASED ON LONG-DISTANCE ATTENTION MODEL RECONSTRUCTION

TECHNICAL FIELD

The invention relates to the technical fields of medical imaging and intelligent image processing, and in particular to a multi-slice magnetic resonance imaging method and a device for implementing the method.

BACKGROUND

Magnetic resonance imaging has great value in clinical disease diagnosis and biomedical research due to the advantages of non-trauma, no ionizing radiation and the like, but the development of the magnetic resonance imaging is hindered by the problems of low imaging speed, overlong scanning time and the like.

A parallel imaging technology, including a recently developed simultaneous multi-slice magnetic resonance technology (which may be considered as 3D-based parallel imaging), reduces the number of spatial encodings in the imaging process and is expected to increase the speed of MRI imaging.

However, parallel imaging data needs to be reconstructed to obtain images. This problem is ill-conditioned. With the increase of the acceleration multiple, it is often accompanied by noise amplification and residual artifacts, which may have potential negative effects on clinical diagnosis and data analysis.

SUMMARY

The main purpose of the present invention is to provide a multi-slice magnetic resonance imaging method based on long-distance attention model reconstruction, which solves the problems of low quality of magnetic resonance images, low diagnosis accuracy, slow imaging speed, and low utilization rate of a magnetic resonance imaging machine in the related art.

Another object of the present invention is to provide a multi-slice magnetic resonance imaging device based on long-distance attention model reconstruction, which solves the problems of low quality of magnetic resonance images, low diagnosis accuracy, slow imaging speed, and low utilization rate of a magnetic resonance imaging machine in the related art.

In order to achieve the above main purpose, the present invention provides a multi-slice magnetic resonance imaging method based on long-distance attention model reconstruction, which may include that: a deep learning reconstruction model is constructed; data preprocessing is performed on multiple slices of simultaneously acquired signals, and multiple slices of magnetic resonance images or K-space data is used as data input; learnable positional embedding and imaging parameter embedding are acquired; the preprocessed input data, the positional embedding and the imaging parameter embedding are input into the deep learning reconstruction model; and the deep learning reconstruction model outputs a result of the magnetic resonance reconstruction image.

In a further solution, the operation that the preprocessed input data, the positional embedding and the imaging parameter embedding are input into the deep learning reconstruction model may include that: the deep learning reconstruction model is of a Transformer structure, and the Transformer structure takes a Transformer codec as a core and includes a front convolutional slice, a rear convolutional slice, and the learnable positional embedding and imaging parameter embedding; after acquiring the learnable positional embedding and imaging parameter embedding, the preprocessed data and the learnable positional embedding are added and input into a Transformer encoder of the deep learning reconstruction model; the output of the Transformer encoder and the learnable imaging parameter embedding are input into a Transformer decoder of the deep learning reconstruction model; and the result of the magnetic resonance reconstruction image is output.

In a further solution, the operation that when the multiple slices of magnetic resonance images are used as the data input, multiple slices of images are represented using a two-dimensional matrix may include that: a zero value is inserted into K-space along a magnetic resonance readout direction, the Field of View (FOV) in the magnetic resonance readout direction is enlarged, and then fast Fourier transform is performed to obtain a slice-aliasing image connected along the magnetic resonance readout direction; and features of the image are extracted using multiple two-dimensional convolutional slices to form a feature tensor, and the feature tensor is divided into patches.

In a further solution, the operation that the preprocessed data and the learnable positional embedding are added and input into a Transformer encoder of the deep learning reconstruction model may include that: the conventional slice unfolds each patch in the form of one-dimensional data, which is added to the learnable positional embedding and input into the Transformer encoder.

In a further solution, the positional embedding is obtained by transforming the coordinates of the patch through a learnable embedding slice; or the positional embedding is obtained by transforming the coordinates of the patch through a fully connected slice.

In a further solution, the operation that the output of the Transformer encoder and the learnable imaging parameter embedding are input into a Transformer decoder of the deep learning reconstruction model may include that: the output of the Transformer encoder and the learnable imaging parameter embedding are input into the Transformer decoder together, the output of the Transformer decoder is rearranged to form another feature tensor, and then multiple reconstructed slice images are generated through the convolutional slice. Herein, the Transformer encoder may include a self-attention slice and a fully connected slice which are configured to calculate all embedding correlations.

In a further solution, the operation that the imaging parameter embedding is acquired may include that: imaging information is scanned, the scanned imaging information is encoded into a vector, and the vector is input into the embedding slice or the fully connected slice or constructed in a fixed manner. Herein, the imaging information may include imaging parts, angles of slices, an acquisition acceleration multiple, a direction and a distance of controllable aliasing, a used sequence type, a direction of phase coding, FOV, TR (Time of Repetition), TE (Time of Echo), a pulse flip angle, a scanned object and a scanning machine.

In a further solution, the operation that the preprocessed input data, the positional embedding and the imaging parameter embedding are input into the deep learning reconstruction model may include that: an original image or K-space data, the imaging parameter embedding and the positional embedding are used as three inputs. Herein, the deep learning reconstruction model may include the convolutional slice and the fully connected slice. The original image or K-space data is processed by multiple conventional slices to form N1 feature channels. The imaging parameter embedding is processed by multiple conventional slices to form N2 feature channels. After splicing, the N1 feature channels and the N2 feature channels are sent to multiple convolutional slices to form N3 feature channels. The positional embedding passes through the fully connected slice to form N3 output values, and the N3 output values are added to the N3 feature channels to be processed by the conventional neural network, thereby obtaining an output result of the magnetic resonance reconstruction image.

In a further solution, the constructed deep learning reconstruction model is combined with gradient-based data consistency updating, and end-to-end iterative training is performed to obtain an optimal output result of the magnetic resonance reconstruction image.

In order to achieve another purpose, the invention provides a multi-slice magnetic resonance imaging device based on long-distance attention model reconstruction, which may include: a model construction unit, configured to construct a deep learning reconstruction model; a data preprocessing unit, configured to perform data preprocessing on multiple slices of simultaneously acquired signals, and use multiple slices of magnetic resonance images or K-space data as data input; an embedding unit, configured to acquire learnable positional embedding and imaging parameter embedding; an image reconstruction unit, configured to input the preprocessed input data, the positional embedding and the imaging parameter embedding into the deep learning reconstruction model; and an output unit, configured to output a result of the magnetic resonance reconstruction image.

It can be seen that the present invention uses a deep learning image reconstruction model, and adds the imaging parameter embedding and spatial positional embedding. For the prior information of imaging (for example, the imaging part, the used sequence, and the like) and long-distance related information in magnetic resonance data, the method provided by the invention may efficiently model and better learn magnetic resonance domain knowledge to improve the problems of noise and artifact of the magnetic resonance reconstruction images.

Therefore, the invention may improve the quality of the magnetic resonance image, improve the diagnosis accuracy of a doctor, increase the imaging speed, improve the utilization rate of a magnetic resonance machine, has a wide application range, does not need to fully mine the center of the K-space, and is widely applicable to gradient echo, spin echo, echo planar and other imaging methods.

The invention will further be described below in combination with the drawings and the embodiments.

DETAILED DESCRIPTION OF THE EMBODIMENTS

In order to make the purposes, technical solutions and advantages of the embodiments of the invention clearer, the technical solutions in the embodiments of the invention will be clearly and completely described below in combination with the drawings in the embodiments of the invention, and it is apparent that the described embodiments are only a part rather all of embodiments of the invention. All other embodiments obtained by those of ordinary skill in the art based on the described embodiments of the invention without creative efforts shall fall within the protection scope of the invention.

A first embodiment of a multi-slice magnetic resonance imaging method based on long-distance attention model reconstruction is as follows.

Figure 1:
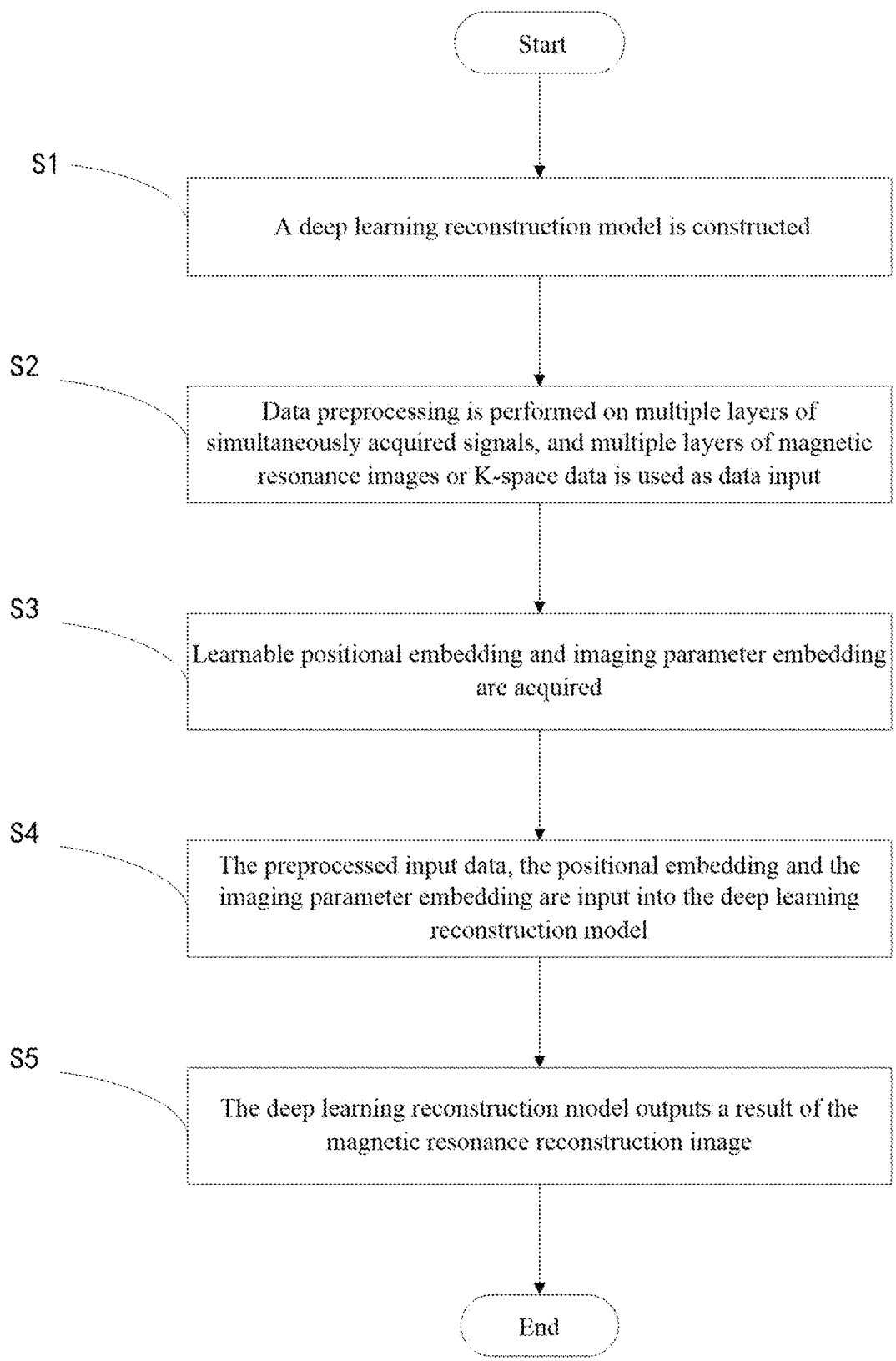
FIG. 1 is a flowchart of a first embodiment of a multi-slice magnetic resonance imaging method based on long-distance attention model reconstruction of the invention.

Referring to FIG. 1, a multi-slice magnetic resonance imaging method based on long-distance attention model reconstruction includes the following steps.

At S1, a deep learning reconstruction model is constructed.

At S2, data preprocessing is performed on multiple slices of simultaneously acquired signals, and multiple slices of magnetic resonance images or K-space data is used as data input.

At S3, learnable positional embedding and imaging parameter embedding are acquired.

At S4, the preprocessed input data, the positional embedding and the imaging parameter embedding are input into the deep learning reconstruction model.

At S5, the deep learning reconstruction model outputs a result of the magnetic resonance reconstruction image.

In the embodiment, the operation that the preprocessed input data, the positional embedding and the imaging parameter embedding are input into the deep learning reconstruction model specifically includes that: the deep learning reconstruction model is of a Transformer structure, and the Transformer structure takes a Transformer codec as a core and includes a front convolutional slice, a rear convolutional slice, and the learnable positional embedding and imaging parameter embedding; after acquiring the learnable positional embedding and imaging parameter embedding, the preprocessed data and the learnable positional embedding are added and input into a Transformer encoder of the deep learning reconstruction model; the output of the Transformer encoder and the learnable imaging parameter embedding are input into a Transformer decoder of the deep learning reconstruction model; and the result of the magnetic resonance reconstruction image is output.

In S2, the operation that when the multiple slices of magnetic resonance images are used as the data input, multiple slices of images are represented using a two-dimensional matrix includes that: a zero value is inserted into a K-space along a magnetic resonance readout direction, the FOV in the magnetic resonance readout direction is enlarged, and then fast Fourier transform is performed to obtain a slice-aliasing image connected along the magnetic resonance readout direction; and features of the image are extracted using multiple two-dimensional convolutional slices to form a feature tensor, and the feature tensor is divided into patches.

In the embodiment, the operation that the preprocessed data and the learnable positional embedding are added and input into a Transformer encoder of the deep learning reconstruction model includes that: the conventional slice unfolds each patch in the form of one-dimensional data, which is added to the learnable positional embedding and input into the Transformer encoder.

Herein, the positional embedding is obtained by transforming the coordinates of the patch through a learnable embedding slice; or the positional embedding is obtained by transforming the coordinates of the patch through a fully connected slice.

In the embodiment, the operation that the output of the Transformer encoder and the learnable imaging parameter embedding are input into a Transformer decoder of the deep learning reconstruction model specifically includes that: the output of the Transformer encoder and the learnable imaging parameter embedding are input into the Transformer decoder together, the output of the Transformer decoder is rearranged to form another feature tensor, and then multiple reconstructed slice images are generated through the convolutional slice. Herein, the Transformer encoder includes a self-attention slice and a fully connected slice which are configured to calculate all embedding correlations.

In S2, the operation that the imaging parameter embedding is acquired includes that: imaging information is scanned, the scanned imaging information is encoded into a vector, and the vector is input into the embedding slice or the fully connected slice or constructed in a fixed manner. Herein, the imaging information may include imaging parts, angles of slices, an acquisition acceleration multiple, a direction and a distance of controllable aliasing, a used sequence type, a direction of phase coding, FOV, TR, TE, a pulse flip angle, a scanned object and a scanning machine.

In the embodiment, the constructed deep learning reconstruction model is combined with gradient-based data consistency updating, and end-to-end iterative training is performed to obtain an optimal output result of the magnetic resonance reconstruction image. Herein, the gradient-based data may be a conjugate gradient method, a gradient descent method, or some other improved method of iterative solution.

In practical application, the simultaneous multi-slice imaging may be regarded as parallel imaging under a 3D condition, and the reconstruction method suitable for the simultaneous multi-slice imaging may be directly popularized to 2D parallel imaging, so that the method is mainly described below by taking the reconstruction of simultaneous multi-slice imaging as an example.

Figure 2:
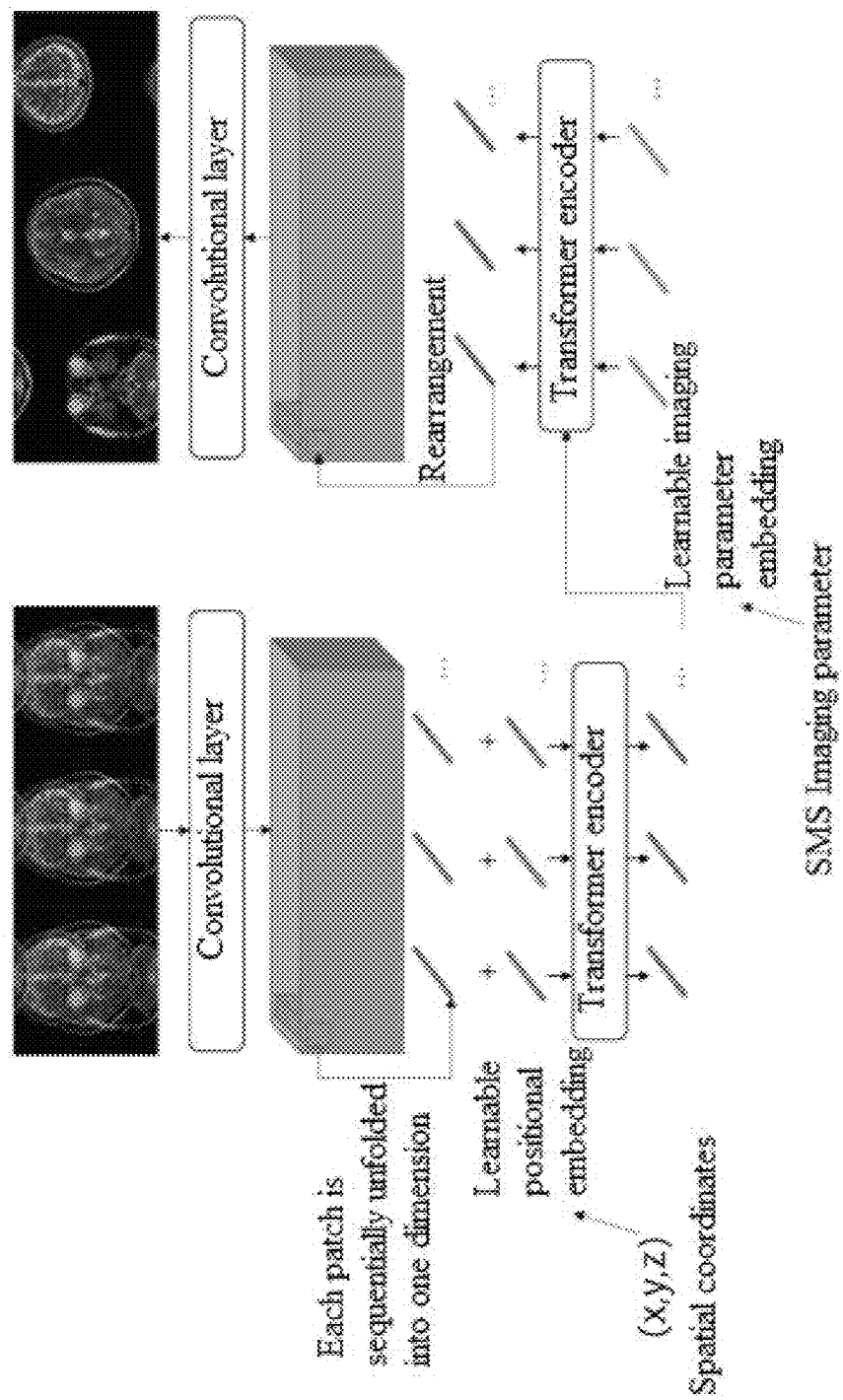
FIG. 2 is a schematic diagram of using a Transformer structure as a deep learning reconstruction model in a first embodiment of a multi-slice magnetic resonance imaging method based on long-distance attention model reconstruction of the invention.

According to the coil sensitivity encoding theory, the reconstruction of simultaneous multi-slice imaging data may correspond to the following optimization problems, such as a formula (1):

$$x_F = \mathrm{argmin}_x \|Ax - b\|^2 + \lambda \|T(x)\|^2 \quad (1)$$

where A is a coding operator corresponding to simultaneous multi-slice sampling and coil sensitivity modulation of the K-space, x is a magnetic resonance image of multiple slices to be reconstructed, b is acquired multi-channel K-space data, and T(x) is regularized constraint. T is realized using the deep learning reconstruction model provided by the embodiment, as shown in FIG. 2, the Transformer codec is taken as the core and a front convolutional slice (Conventional neural Network (CNN)), a rear convolutional slice, and the learnable positional embedding and imaging parameter embedding are included.

In the embodiment, firstly, read-concatenate preprocessing is performed on multiple slices of simultaneously acquired signals, so that multiple slices of magnetic resonance images may be represented by using a two-dimensional matrix, and the specific operations are as follows: the zero value is inserted into the K-space along a magnetic resonance readout direction, the FOV in the magnetic resonance readout direction is enlarged, and then fast Fourier transform is performed to obtain the slice-aliasing image connected along the magnetic resonance readout direction. Then, features of the image are extracted using multiple two-dimensional convolutional slices to form the feature tensor. The feature tensor is divided into small patches (Patch). Each patch is unfolded in one dimension and added to the learnable positional embedding to be input into the Transformer encoder. Of course, in other embodiments, multiple slices of simultaneously acquired K-space (rather than images) may also be taken as input.

In the embodiment, the positional embedding may be obtained by transforming the coordinates (x, y, z) or (kx, ky, kz) of the patch through a learnable embedding slice (for example, tf.nn.embedding lookup in a tensorflow framework). Or, the positional embedding may be obtained by transforming the fully connected slices. Of course, the positional embedding may also be constructed directly in a non-learning fixed manner, for example, sine and cosine encoding.

In the embodiment, the Transformer encoder may refer to implementation in Bidirectional Encoder Representation from Transformers (BERT) (https://github.com/google-research/bert) and includes a self-attention slice and a fully connected slice which are configured to calculate all embedding correlations. The output of the Transformer encoder and the learnable imaging parameter embedding are input to the Transformer decoder together. The output of the Transformer decoder is rearranged to form another feature tensor, and then multiple reconstructed slice images (the offset caused by controllable aliasing may be removed later) are generated through the convolutional slice.

In the embodiment, the manner of acquiring the imaging parameter embedding is as follows: firstly, the imaging information scanned at this time is encoded into the vector, and the vector is input into the embedding slice or the fully connected slice or constructed in a fixed manner.

Herein, the imaging information may include the imaging parts (head, neck, chest, upper abdomen, lower abdomen, elbow joint, knee joint and the like, each of which is represented by an integer), the angles of the slices (represented by included angles with three planes), the acquisition acceleration multiple (typically a decimal number between 1 and 20), the used sequence type (FSE, FLASH, EPI, FLAIR and the like, each of which is represented by an integer), the direction of phase encoding, the FOV (field size), the TR, the TE, the pulse flip angle, the age, gender, height, weight of the scanned object, the field strength of the scanning machine, Brand, model, and the like. Of course, in some embodiments, the information may also be obtained through Digital Imaging and Communications in Medicine (DICOM) file information.

In the embodiment, the input data may be processed by using the deep learning reconstruction model, and the obtained output is the final reconstruction result.

Figure 3:
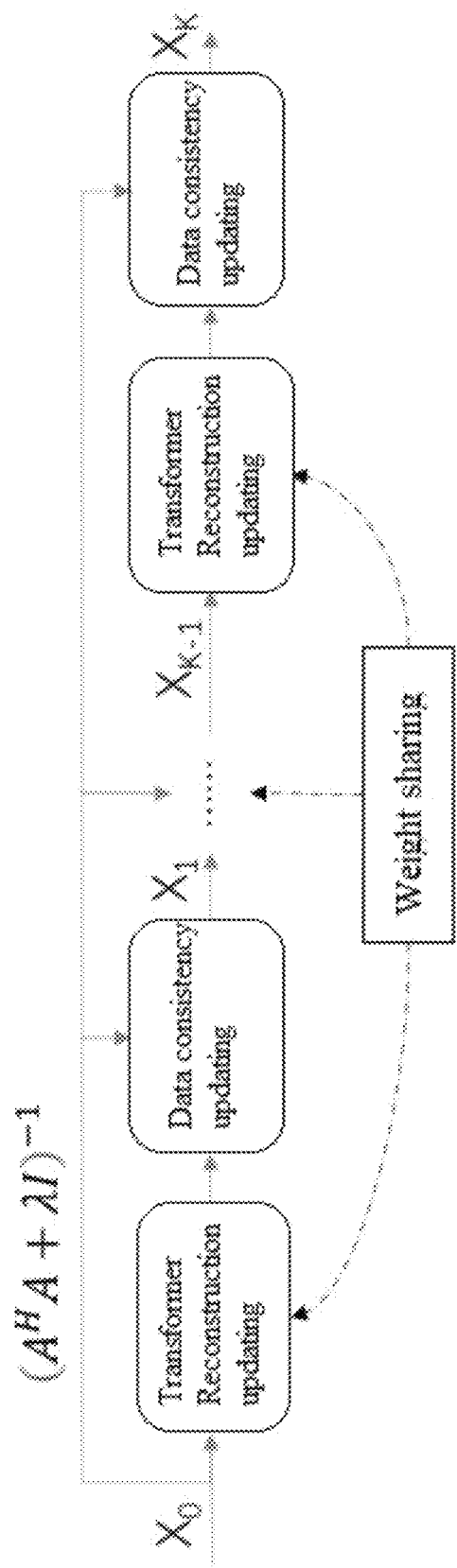
FIG. 3 is a schematic diagram of using a deep learning reconstruction model in an iterative unfolding framework in an embodiment of a multi-slice magnetic resonance imaging method based on long-distance attention model reconstruction of the invention.

In addition, a MoDL reconstruction framework (https://github.com/hkaggarwal/modl) may be combined, the reconstruction model is combined with gradient-based data consistency updating, and end-to-end iterative training is performed to obtain the final output image, as shown in FIG. 3, which may have the advantage that less training data may be used. Of course, the reconstruction model is trained on a training data set no matter what manner is adopted.

The training data set of the embodiment may be obtained in various ways, may be obtained by scanning on a real magnetic resonance machine, may also be obtained from a large-scale public magnetic resonance data set (for example, Alzheimer's Disease Neuroimaging Initiative (ADNI), Human Connectome Project (HCP) and the like), or may also be obtained through algorithm simulation, for example, by a bloch equation or directly using open source magnetic resonance simulation software such as mrilab (http://mrilab.sourceforge.net/). Of course, the three methods may also be used in combination. During training, a weighted-average comprehensive loss function such as L1 loss, L2 loss, perceptual loss, adversarial loss, and the like may be used, and parameter updating may be performed by using an ADAM optimizer.

It can be seen that the present invention uses a deep learning image reconstruction model, and adds the imaging parameter embedding and spatial positional embedding. For the prior information of imaging (for example, the imaging part, the used sequence, and the like) and long-distance related information in magnetic resonance data, the method provided by the invention may efficiently model and better learn magnetic resonance domain knowledge to improve the problems of noise and artifact of the magnetic resonance reconstruction images.

Therefore, the invention may improve the quality of the magnetic resonance image, improve the diagnosis accuracy of the doctor, increase the imaging speed, improve the utilization rate of the magnetic resonance machine, has a wide application range, does not need to fully mine the center of the K-space, and is widely applicable to gradient echo, spin echo, echo planar and other imaging methods.

A second embodiment of the multi-slice magnetic resonance imaging method based on long-distance attention model reconstruction is as follows.

In the embodiment, the operation that the preprocessed input data, the positional embedding and the imaging parameter embedding are input into the deep learning reconstruction model further includes that: an original image or K-space data, the imaging parameter embedding and the positional embedding are used as three inputs. Herein, the deep learning reconstruction model includes a convolutional slice and a fully connected slice. The original image or K-space data is processed by multiple conventional slices to form N1 feature channels. The imaging parameter embedding is processed by multiple conventional slices to form N2 feature channels. After splicing, the N1 feature channels and the N2 feature channels are sent to multiple convolutional slices to form N3 feature channels. The positional embedding passes through the fully connected slice to form N3 output values, and the N3 output values are added to the N3 feature channels to be processed by the conventional neural network, thereby obtaining an output result of the magnetic resonance reconstruction image.

It can be seen that the Transformer structure is not necessary. In the embodiment, only the conventional slice and the fully connected slice may be used. The original image (or the K-space) data, the imaging parameter embedding and the positional embedding are used as three inputs. Herein, the deep learning reconstruction model includes the convolutional slice and the fully connected slice. The original image or K-space data is processed by multiple conventional slices to form N1 feature channels. The imaging parameter embedding is processed by multiple conventional slices to form N2 feature channels. After splicing, the N1 feature channels formed by the original image (or K-space) and the N2 feature channels formed by the imaging parameters are sent to multiple convolutional slices to form N3 feature channels. The positional embedding passes through the fully connected slice to form N3 output values, and the N3 output values are added to the N3 feature channels to be processed by the conventional neural network (for example, resnet50, efficientnet and other structures), thereby obtaining the reconstruction result.

An embodiment of a multi-task-based magnetic resonance reconstruction model training device is as follows.

Figure 4:
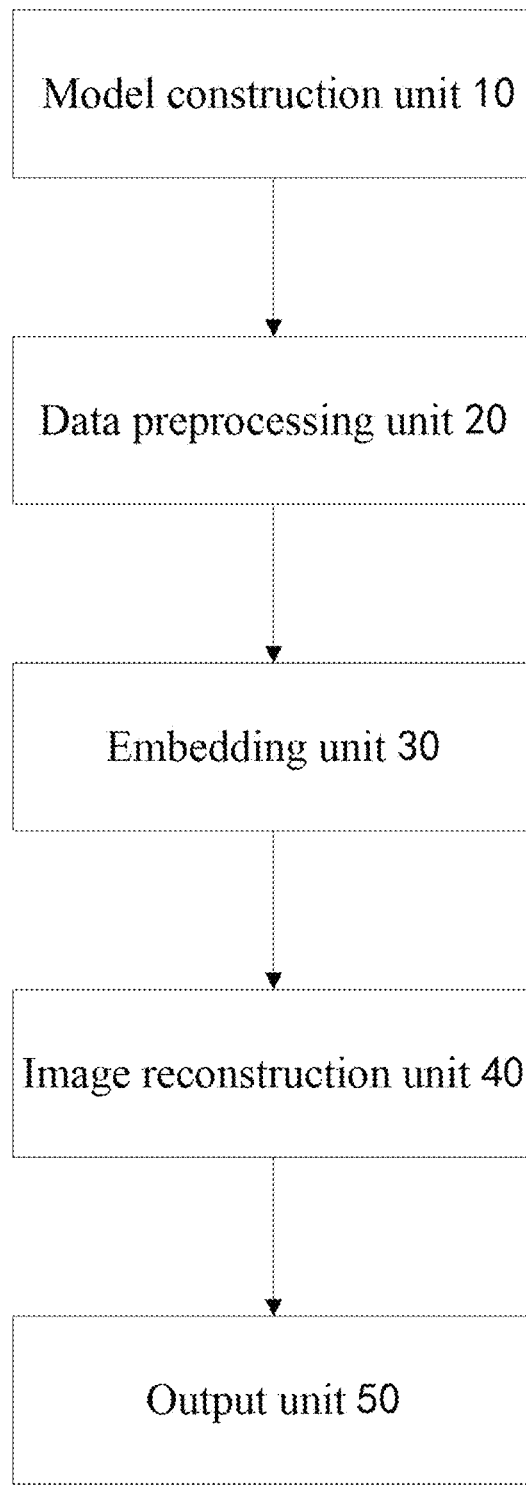
FIG. 4 is a schematic diagram of a multi-slice magnetic resonance imaging device based on long-distance attention model reconstruction of the invention.

As shown in FIG. 4, the invention provides a multi-task-based magnetic resonance reconstruction model training device, which includes: a model construction unit 10, a data preprocessing unit 20, an embedding unit 30, an image reconstruction unit 40 and an output unit 50.

The model construction unit 10 is configured to construct a deep learning reconstruction model.

The data preprocessing unit 20 is configured to perform data preprocessing on multiple slices of simultaneously acquired signals, and use multiple slices of magnetic resonance images or K-space data as data input.

The embedding unit 30 is configured to acquire learnable positional embedding and imaging parameter embedding.

The image reconstruction unit 40 is configured to input the preprocessed input data, the positional embedding and the imaging parameter embedding into the deep learning reconstruction model.

The output unit 50 is configured to output a result of the magnetic resonance reconstruction image.

In the embodiment, the operation that the preprocessed input data, the positional embedding and the imaging parameter embedding are input into the deep learning reconstruction model specifically includes that: the deep learning reconstruction model is of a Transformer structure, and the Transformer structure takes a Transformer codec as a core and includes a front convolutional slice, a rear convolutional slice, and the learnable positional embedding and imaging parameter embedding; after acquiring the learnable positional embedding and imaging parameter embedding, the preprocessed data and the learnable positional embedding are added and input into a Transformer encoder of the deep learning reconstruction model; the output of the Transformer encoder and the learnable imaging parameter embedding are input into a Transformer decoder of the deep learning reconstruction model; and the result of the magnetic resonance reconstruction image is output.

Herein, the operation that when the multiple slices of magnetic resonance images are used as the data input, multiple slices of images are represented using a two-dimensional matrix includes that: a zero value is inserted into K-space along a magnetic resonance readout direction, the FOV in the magnetic resonance readout direction is enlarged, and then fast Fourier transform is performed to obtain a slice-aliasing image connected along the magnetic resonance readout direction; and features of the image are extracted using multiple two-dimensional convolutional slices to form a feature tensor, and the feature tensor is divided into patches.

In the embodiment, the operation that the preprocessed data and the learnable positional embedding are added and input into a Transformer encoder of the deep learning reconstruction model includes that: the conventional slice unfolds each patch in the form of one-dimensional data, which is added to the learnable positional embedding and input into the Transformer encoder.

Herein, the positional embedding is obtained by transforming the coordinates of the patch through a learnable embedding slice; or the positional embedding is obtained by transforming the coordinates of the patch through a fully connected slice.

In the embodiment, the operation that the output of the Transformer encoder and the learnable imaging parameter embedding are input into a Transformer decoder of the deep learning reconstruction model specifically includes that: the output of the Transformer encoder and the learnable imaging parameter embedding are input into the Transformer decoder together, the output of the Transformer decoder is rearranged to form another feature tensor, and then multiple reconstructed slice images are generated through the convolutional slice. Herein, the Transformer encoder may include a self-attention slice and a fully connected slice which are configured to calculate all embedding correlations.

Herein, the operation that the imaging parameter embedding is acquired includes that: imaging information is scanned, the scanned imaging information is encoded into a vector, and the vector is input into the embedding slice or the fully connected slice or constructed in a fixed manner. Herein, the imaging information may include imaging parts, angles of slices, an acquisition acceleration multiple, a direction and a distance of controllable aliasing, a used sequence type, a direction of phase coding, FOV, TR, TE, a pulse flip angle, a scanned object and a scanning machine.

In the embodiment, the constructed deep learning reconstruction model is combined with gradient-based data consistency updating, and end-to-end iterative training is performed to obtain an optimal output result of the magnetic resonance reconstruction image.

An embodiment of a computer device is as follows.

A computer device in the embodiment includes a processor. When executing a computer program, the processor implements the steps in the embodiment of the multi-slice magnetic resonance imaging method.

For example, the computer program may be divided into one or more modules, and the one or more modules are stored in a memory and executed by the processor to complete the present invention. One or more modules may be a series of computer program instruction segments capable of performing specific functions, and the instruction segments are configured to describe the execution process of the computer program in the computer device.

The computer device may include, but is not limited to, the processor and the memory. Those skilled in the art may understand that the computer device may include more or fewer components, or combine certain components, or different components. For example, the computer device may also include input and output devices, a network access device, a buses, and the like.

For example, the processor may also be a Central Processing Unit (CPU), or another general-purpose processor, a Digital Signal Processor (DSP), an Application Specific Integrated Circuit (ASIC), a Field Programmable Gate Array (FPGA) or other programmable logic devices, a discrete gate or transistor logic device, or a discrete hardware component. The general-purpose processor may be a microprocessor, or the processor may be any conventional processor or the like. The processor is a control center of the computer device and is connected with each part of the whole computer device through various interfaces and lines.

The memory may be configured to store the computer program and/or module, and the processor implements various functions of a long-time scale power balance check and big data analysis apparatus by running or executing the computer program and/or module stored in the memory and calling the data stored in the memory. For example, the memory may mainly include a program storage area and a data storage area. Herein, the program storage area may store an operating system, an application program required for at least one function (for example, a sound receiving function, a sound-to-text function, and the like), and the like. The data storage area may store data (for example, audio data, text data, and the like) created according to the use of the mobile phone, and the like. In addition, the memory may include a high-speed random access memory and may also include a non-volatile memory, for example, a hard disk, a memory, a plug-in hard disk, a Smart Media Card (SMC), a Secure Digital (SD) card, a Flash Card, at least one magnetic disk storage device, a flash memory device, or other volatile solid-state storage device.

An embodiment of a storage medium is as follows.

A module integrated by a terminal device may be stored in a computer-readable storage medium if being implemented in the form of a software functional unit and sold or used as an independent product. Based on such an understanding, all or part of the processes in the embodiment method are implemented in the invention, which may also be completed by instructing related hardware through a computer program. The computer program may be stored in a computer-readable storage medium, and when executed by a processor, the computer program may implement the steps of the above method embodiments.

Herein, the computer program includes a computer program code, and the computer program code may be in the form of source code, object code, executable file or some intermediate form. The computer readable medium may include: any entity or apparatus capable of carrying the computer program code, a recording medium, a U disk, a removable hard disk, a magnetic disk, an optical disk, a computer memory, a Read Only Memory (ROM), a Random Access Memory (RAM), an electrical carrier signal, a telecommunication signal, a software distribution medium, and the like. It is to be noted that the contents contained in the computer-readable medium may be appropriately increased or decreased according to the requirements of legislation and patent practice in jurisdictions. For example, in some jurisdictions, according to legislation and patent practice, the computer-readable medium does not include the electrical carrier signal and the telecommunication signal.

It can be seen that the present invention provides a computer device and a storage medium, which may include: one or more memories, one or more processors. The memory is configured to store program codes and intermediate data generated in a program running process, store a model output result and store a model and model parameters. The processor is configured to process processor resources occupied by code operation and multiple processor resources occupied during model training.

It is to be noted that the above are only preferred embodiments of the present invention, but the design concept of the invention is not limited thereto, and any non-substantial modification made to the present invention by using this concept also falls within the protection scope of the present invention.

What is claimed is:

1. A multi-slice magnetic resonance imaging method based on long-distance attention model reconstruction, comprising:
   constructing a deep learning reconstruction model;
   performing data preprocessing on multiple slices of simultaneously acquired signals, and using multiple slices of magnetic resonance images or K-space data as data input;
   acquiring learnable positional embedding and imaging parameter embedding;
   inputting the preprocessed input data, the positional embedding and the imaging parameter embedding into the deep learning reconstruction model, wherein the deep learning reconstruction model is of a Transformer structure, and the Transformer structure takes a Transformer codec as a core and comprises a front convolutional slice, a rear convolutional slice, and the learnable positional embedding and imaging parameter embedding;
   adding and inputting, after acquiring the learnable positional embedding and imaging parameter embedding, the preprocessed data and the learnable positional embedding into a Transformer encoder of the deep learning reconstruction model;
   inputting the output of the Transformer encoder and the learnable imaging parameter embedding into a Transformer decoder of the deep learning reconstruction model; and
   outputting, by the deep learning reconstruction model, a result of the magnetic resonance reconstruction image.

2. The multi-slice magnetic resonance imaging method of claim 1, wherein
   when the multiple slices of magnetic resonance images are used as the data input, representing multiple slices of images using a two-dimensional matrix comprises:
   inserting a zero value in K-space along a magnetic resonance readout direction, enlarging the Field of View (FOV) in the magnetic resonance readout direction, and then performing fast Fourier transform to obtain a slice-aliasing image connected along the magnetic resonance readout direction; and
   extracting features of the image using multiple two-dimensional convolutional slices to form a feature tensor, and dividing the feature tensor into patches.

3. The multi-slice magnetic resonance imaging method of claim 2, wherein adding and inputting the preprocessed data and the learnable positional embedding into a Transformer encoder of the deep learning reconstruction model comprises:
   unfolding, by the conventional slice, each patch in the form of one-dimensional data, which is added to the learnable positional embedding and input into the Transformer encoder.

4. The multi-slice magnetic resonance imaging method of claim 3, wherein
   the positional embedding is obtained by transforming the coordinates of the patch through a learnable embedding slice; or
   the positional embedding is obtained by transforming the coordinates of the patch through a fully connected slice.

5. The multi-slice magnetic resonance imaging method of claim 4, wherein inputting the output of the Transformer encoder and the learnable imaging parameter embedding into a Transformer decoder of the deep learning reconstruction model comprises:
   inputting the output of the Transformer encoder and the learnable imaging parameter embedding into the Transformer decoder together, rearranging the output of the Transformer decoder to form another feature tensor, and then generating multiple reconstructed slice images through the convolutional slice, wherein the Transformer encoder comprises a self-attention slice and a fully connected slice which are configured to calculate all embedding correlations.

6. The multi-slice magnetic resonance imaging method of claim 5, wherein
   acquiring the imaging parameter embedding comprises: scanning imaging information, encoding the scanned imaging information into a vector, and inputting the vector into the embedding slice or the fully connected slice or constructing in a fixed manner;
   wherein the imaging information comprises imaging parts, angles of slices, an acquisition acceleration multiple, a direction and a distance of controllable aliasing, a used sequence type, a direction of phase coding, FOV, Time of Repetition (TR), Time of Echo (TE), a pulse flip angle, a scanned object and a scanning machine.

7. The multi-slice magnetic resonance imaging method of claim 1, wherein inputting the preprocessed input data, the positional embedding and the imaging parameter embedding into the deep learning reconstruction model comprises:
   using an original image or K-space data, the imaging parameter embedding and the positional embedding as three inputs, wherein the deep learning reconstruction model comprises the convolutional slice and the fully connected slice;
   processing, by the multiple conventional slices, the original image or K-space data to form N1 feature channels;
   processing, by the multiple conventional slices, the imaging parameter embedding to form N2 feature channels;
   sending, after splicing, the N1 feature channels and the N2 feature channels to multiple convolutional slices to form N3 feature channels; and
   enabling the positional embedding to pass through the fully connected slice to form N3 output values, and adding the N3 output values to the N3 feature channels to be processed by the conventional neural network, thereby obtaining an output result of the magnetic resonance reconstruction image.

8. The multi-slice magnetic resonance imaging method of claim 1, wherein
   the constructed deep learning reconstruction model is combined with gradient-based data consistency updating, and end-to-end iterative training is performed to obtain an optimal output result of the magnetic resonance reconstruction image.

9. The multi-slice magnetic resonance imaging method of claim 2, wherein
   the constructed deep learning reconstruction model is combined with gradient-based data consistency updating, and end-to-end iterative training is performed to obtain an optimal output result of the magnetic resonance reconstruction image.

10. The multi-slice magnetic resonance imaging method of claim 3, wherein
    the constructed deep learning reconstruction model is combined with gradient-based data consistency updating, and end-to-end iterative training is performed to obtain an optimal output result of the magnetic resonance reconstruction image.

11. The multi-slice magnetic resonance imaging method of claim 4, wherein the constructed deep learning reconstruction model is combined with gradient-based data consistency updating, and end-to-end iterative training is performed to obtain an optimal output result of the magnetic resonance reconstruction image.

12. The multi-slice magnetic resonance imaging method of claim 5, wherein
the constructed deep learning reconstruction model is combined with gradient-based data consistency updating, and end-to-end iterative training is performed to obtain an optimal output result of the magnetic resonance reconstruction image.

13. The multi-slice magnetic resonance imaging method of claim 6, wherein
the constructed deep learning reconstruction model is combined with gradient-based data consistency updating, and end-to-end iterative training is performed to obtain an optimal output result of the magnetic resonance reconstruction image.

14. The multi-slice magnetic resonance imaging method of claim 7, wherein
the constructed deep learning reconstruction model is combined with gradient-based data consistency updating, and end-to-end iterative training is performed to obtain an optimal output result of the magnetic resonance reconstruction image.

15. A multi-slice magnetic resonance imaging device based on long-distance attention model reconstruction, comprising:

a model construction unit, configured to construct a deep learning reconstruction model;

a data preprocessing unit, configured to perform data preprocessing on multiple slices of simultaneously acquired signals, and use multiple slices of magnetic resonance images or K-space data as data input;

an embedding unit, configured to acquire learnable positional embedding and imaging parameter embedding;

an image reconstruction unit, configured to input the preprocessed input data, the positional embedding and the imaging parameter embedding into the deep learning reconstruction model, wherein the deep learning reconstruction model is of a Transformer structure, and the Transformer structure takes a Transformer codec as a core and comprises a front convolutional slice, a rear convolutional slice, and the learnable positional embedding and imaging parameter embedding; add and input, after acquiring the learnable positional embedding and imaging parameter embedding, the preprocessed data and the learnable positional embedding into a Transformer encoder of the deep learning reconstruction model; and input the output of the Transformer encoder and the learnable imaging parameter embedding into a Transformer decoder of the deep learning reconstruction model; and an output unit, configured to output a result of the magnetic resonance reconstruction image.

* * * * *